(12) United States Patent
Bergens et al.

(10) Patent No.: US 6,371,939 B2
(45) Date of Patent: Apr. 16, 2002

(54) AUTOINJECTOR

(75) Inventors: Thomas Bergens, Ingarö ; Mikael Amark, Brottby, both of (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/768,761

(22) Filed: Jan. 24, 2001

Related U.S. Application Data (63) Continuation of application No. 09/411,954, filed on Oct. 4, 1999, now Pat. No. 6,270,479
(60) Provisional application No. 60/107,851, filed on Nov. 10, 1998.

(30) Foreign Application Priority Data

Oct. 26, 1998 (SE) ................................. 9803662

(51) Int. Cl.$^7$ ................................. A61M 5/20
(52) U.S. Cl. ................................. 604/156
(58) Field of Search ................................. 604/131, 154, 604/95.01, 95.02, 110, 130, 132, 133, 134, 135, 136, 138, 139, 156–158, 192–196, 198, 199, 218, 232; 606/172, 182; 128/DIG. 1, DIG. 12, DIG. 13

(56) References Cited

U.S. PATENT DOCUMENTS

| | | |
|---|---|---|
| 3,279,653 A | 10/1966 | Pfleger |
| 3,474,787 A | 10/1969 | Grant |
| 3,605,745 A | 9/1971 | Hodosh |
| 3,797,489 A | 3/1974 | Sarnoff |
| 3,886,938 A | 6/1975 | Szabo et al. |
| 4,430,079 A | 2/1984 | Thill et al. |
| 4,437,859 A | 3/1984 | Whitehouse et al. |
| 4,652,260 A | 3/1987 | Fenton, Jr. et al. |
| 4,838,857 A | 6/1989 | Strowe et al. |
| 4,976,696 A | 12/1990 | Sanderson et al. |
| 5,034,004 A | 7/1991 | Crankshaw |
| 5,300,030 A | 4/1994 | Crossman et al. |
| 5,545,140 A | 8/1996 | Conero et al. |
| 5,843,036 A | 12/1998 | Olive et al. |

FOREIGN PATENT DOCUMENTS

| | | |
|---|---|---|
| DE | 3914818 | 11/1990 |
| GB | 1026593 | 7/1962 |
| WO | WO 8810129 | 12/1988 |
| WO | WO 9413342 | 6/1994 |
| WO | WO 9504562 | 2/1995 |
| WO | WO 9531235 | 11/1995 |

*Primary Examiner*—Manuel Mendez
(74) *Attorney, Agent, or Firm*—Dinsmore & Shohl LLP

(57) ABSTRACT

An autoinjector for replaceable containers of syringe type, comprising a barrel of axially roughly constant cross-section, a front opening with or for an injection needle and at least one movable rear piston, optionally with a plunger connected thereto, inserted in the barrel for the displacement of a container content, the autoinjector comprising a) a housing, b) a container carrier, arranged for reception of the container and arranged movably in relation to the housing in container axial direction between a rear, needle-covering, position and a forward, needle-exposing, position, c) an autopenetration mechanism, comprising at least a penetration head and a penetration drive, the penetration head being arranged for movement of the barrel or carrier in the forward direction and the penetration drive being operable to apply force between the housing and the penetration head, d) an autoinjection mechanism, comprising at least an injection head and an injection drive, the injection head being arranged for movement of the piston or plunger in the forward direction and the injection drive being operable to apply force between the housing or the carrier and the injection head, e) optionally an autoreturn mechanism operable to apply force between the housing and the barrel or carrier for movement thereof in the rearward direction and f) a control system for sequencing the operation of at least the autopenetration and autoinjection mechanisms, at least comprising a releasable penetration lock for the autopenetration mechanism and a releasable injection lock for the autoinjection mechanism. The carrier is designed to accommodate either of at least two containers of different length and/or width and at least one damper arranged for energy absorption from the autopenetration and/or autoinjection movement.

13 Claims, 9 Drawing Sheets

AUTOINJECTOR

This application is a continuation of application Ser. No. 09/411,954, filed Oct. 4, 1999, now U.S. Pat. No. 6,270,479 which claim benefit of 60/107,851 filed Nov. 10, 1998.

TECHNICAL FIELD

An autoinjector for replaceable containers of syringe type, comprising a barrel of axially roughly constant cross-section, a front opening with or for an injection needle and at least one movable rear piston, optionally with a plunger connected thereto, inserted in the barrel for the displacement of a container content, the autoinjector comprising a) a housing, b) a container carrier, arranged for reception of the container and arranged movably in relation to the housing in container axial direction between a rear, needle-covering, position and a forward, needle-exposing, position, c) an autopenetration mechanism, comprising at least a penetration head and a penetration drive, the penetration head being arranged for movement of the barrel or carrier in the forward direction and the penetration drive being operable to apply force between the housing and the penetration head, d) an autoinjection mechanism, comprising at least an injection head and an injection drive, the injection head being arranged for movement of the piston or plunger in the forward direction and the injection drive being operable to apply force between the housing or the carrier and the injection head, e) optionally an autoreturn mechanism operable to apply force between the housing and the barrel or carrier for movement thereof in the rearward direction and f) a control system for sequencing the operation of at least the autopenetration and autoinjection mechanisms, at least comprising a releasable penetration lock for the autopenetration mechanism and a releasable injection lock for the autoinjection mechanism.

BACKGROUND

Autoinjectors are designed to facilitate injection procedures over those required by manual use of common syringes and to secure a proper injection result highly independent of operational circumstances. Autoinjectors are typically used in non-hospital environments, sometimes in emergency situations, and by non-professionals like unskilled assistants or the patients themselves, which operator groups may include sick, disabled, elderly and child persons. The autoinjectors provide at least an automatic injection step in which stored energy, for example from a compressed spring, is released by a trigger to act on a syringe piston or plunger for expulsion of syringe content. Frequently the autoinjectors also provide an automatic penetration step in which stored energy is used for propulsion of the syringe from a rear position, in which the needle is hidden, to a front position, in which the needle is at least partially exposed, to thereby relieve the patient from the, sometimes fearful, task of inserting the needle through the skin and to secure an always appropriate penetration depth once the autoinjector front has been placed against the skin. Autopenetration and autoinjection may take place concurrently, e.g. in simple devices or for the intentional purpose of allowing for an over depth distributed injection. Normally it is desirable to limit injection until the needle has reached or is close to its target location. Still some known injectors try to obtain this feat with a single force system acting on syringe piston or plunger for both purposes, relying for sequencing on the normally lower needle penetration resistance than fluid ejection flow resistance. Yet impact, propulsion inertia and friction cannot prevent at least some leakage during penetration but above all, in case the penetration movement is prevented or jams, injection will entirely fail with preparation expelled on the skin or at improper depth. Hence more advanced injectors applies penetration force directly or indirectly on the syringe barrel, with single or dual drive systems, which requires some control mechanism disabling injection force application during most of the penetration phase and enabling injection force only after proper penetration. Autoinjectors may also provide an automatic needle retraction step in which stored energy, typically stored during the penetration movement in a weaker return counterspring, acts to push the syringe back into the autoinjector after completed injection in order to relieve the user from the task and risk of withdrawal, to verify sequence completion to the user and to prevent inadvertent needle pricks after use. Again, this function may need a control mechanism enabling action of the return spring only after completed injection, normally accomplished by separation of the penetration and injection forces from the syringe at a certain forward extreme for the piston or plunger, freeing the return spring for action.

Most known autoinjectors are designed for use with a single syringe type or even a single specialized and adapted syringe type container in order to meet the various tolerance in dimensions, sizes and forces involved and these requirements become more pronounced when more of the advanced features outlined above are included in the injector. Yet there is a need for autoinjectors able to operate with a variety of syringe sizes, filling degrees, preparation viscosities, aging properties, temperature conditions, needles and flow characteristics. A manufacturer of a broad range of preparations may need a device useful for many container types and doses. Low cost preparations in particular cannot support development of a unique device or syringe container of its own and furthermore may require use of cheap standardized syringe types on the market with a selected minimum size for each dose. Patients on prescription of several pharmaceuticals may benefit from replacement of several devices for a single universal one. Manufacturers of injectors may find a broader market for their autoinjectors if compatible with container variations.

The above objects meet with numerous problems. Variations in size first require a syringe seat or carrier, not only able to accommodate and guide the various container movements with small lateral deviations, but also to secure appropriate start and end positions with respect to both the injector front and the injector mechanism. Variations in length or filling degree means differences in start positions for penetration and injection, either requiring a complicated device with adaptable start positions or long worst case dead runs for the mechanism, creating strong and potentially destructive impact forces or painful injection rates. The force requirements are highly variable. Variations in diameter, for example, means variations in injection force due to differences in piston cross-section surface, even at similar hydraulic flow pressures, as well as differences in piston to wall friction. Further broadening in force requirements is caused by differences in flow characteristics, such as resistance and obstructions in syringe opening, needle lengths or diameters as well as receiving tissue, and by differences in piston to wall friction, even at constant diameter, due to manufacturing tolerances and aging, typically resulting in increased friction due to an ongoing depletion of lubricant in the piston to wall contact surface. It is also well known that the first piston displacement requires a much higher "break-loose" force than continued motion. An again increased force may be desirable at the piston bottoming out to fully squeeze out container content, of special value at precise dosing or for expensive preparations. If the autoinjector drive systems are proportioned for the highest force required by all the abovesaid factors combined, they tend to be excessively strong for less demanding combinations, besides becoming generally bulky and ungainly. Applied in the penetration step the forces may damage or destroy smaller or weaker glass containers and counteract a safe penetration due to vibrations, shaking, recoil and rebound effects. Applied to the injection step extreme pressures may damage the container itself, deform the piston or blow away front sealing or attachments and most probably cause pain and bruises in the receiving tissue. As indicated above all these problems are exaggerated if the high forces are combined with inertia effects from substantial mechanism dead run. If, on the other hand, the autoinjector is provided with means for adjusting the force to the requirements of each container type, these problems can be reduced but instead a more complicated device results and an additional tuning step is expected of the user, defeating the basic simplicity, safety and rapidity reasons for using autoinjectors. Finally, a variety of container types, sizes and tolerances place severe demands on the control mechanism for sequencing the autoinjector phases, as the containers may require different locations and conditions for shift between enabled and disabled states.

Existing prior art does not seem to give much guidance to the resolution of the abovesaid problems. Infusion pumps, typically for slow speed administration in hospital settings, explicitly usable for syringes of different sizes are known, as exemplified by U.S. Pat. No. 4,652,260, U.S. Pat. No. 4,838,857, U.S. Pat. No. 4,976,696, U.S. Pat. No. 5,034,004 and U.S. Pat. No. 5,545,140, all relating to injection by electric motor means where speed can easily be controlled. Similar infusion pumps using mechanical drive means under hydraulic speed control are known from U.S. Pat. No. 3,474,787, U.S. Pat. No. 3,605,745, U.S. Pat. No. 4,430,079, U.S. Pat. No. 4,437,859, WO 88/10129 and GB 1,026,593 or under mechanical speed control from U.S. Pat. No. 3,279, 653 and U.S. Pat. No. 3,886,938, although these references do not suggest any adaptations for syringes of varying size. Common to all infusion pump systems is that no penetration step is involved, and still less an autopenetration step, or any needle return step. Accordingly they provide no solutions in this regard or in connection with sequencing such steps. Nor are any solutions to be found in respect of the abovesaid force problems, due to the slow speeds and flow pressures involved and due to the common practice of initiating the infusion procedure by manually or automatically placing driver heads cautiously against the syringe plunger. Any overpressure arises so slowly that the infusion procedure easily can be halted, automatically or manually after delivery of an alarm signal.

Some autoinjector proposals try to cope with excessive forces by including mechanical dampers in the form of impact retarding springs, elastic gaskets etc., as exemplified by WO 94/13342, WO 95/04562 and DE 3,914,818. These proposals are not made for the purpose of allowing syringe variations and are entirely unsatisfactory and insufficient for the dramatically broadened force requirements in these connections. Also the other problems described are left unsolved.

The WO 95/31235 reference discloses an autoinjector which can be used with syringe subassemblies of different sizes and of standard type, having plunger shafts. However, no solution of general nature is given. For each type an adapted medical module has to be provided and the problem of allowing for different sized syringes in a common carrier is not addressed and expulsion of different doses require special stop surface arrangements in the modules. Further, no solution is given for such arrangements in connection with autopenetration force applied to the syringe barrel rather than its shaft or for automatic needle return. The arrangements described are unable to handle problems with high and varying injection forces.

Accordingly there remains a need for autoinjector designs better adapted for use with great variations in syringe size and type and with improved capabilities for handling the problems outlined.

THE INVENTION GENERALLY

A main object of the present invention is to provide an autoinjector avoiding or ameliorating the above described problems. A more specific object is to provide an autoinjector adapted for use with container variations as outlined. Another object is to provide an autoinjector able to perform its functions within a broad range of injection force requirements. A further object is to provide such an autoinjector with controlled injection speed. Another object is to offer an autoinjector able to secure complete emptying of containers. Still another object is to provide such autoinjectors highly compatible with autopenetration and autoreturn functions. Yet another object is to offer an autoinjector compatible with autopenetration forces applied to container barrel rather than its piston. A further object is to provide an autoinjector able to sequence the operation phases with a common control mechanism. Still another object is to offer such autoinjectors requiring no more user actions on the device than charging, cocking and triggering.

These objects are reached with the characteristics set forth in the appended patent claims.

By including in the autoinjector a container carrier designed to accommodate containers of different widths and/or lengths the device is usable for a broad range of containers without need for exchange of insertions or other adaptive actions from the user. Variations in length also accounts for variations in filling degree, especially in connection with syringe type containers having a plunger of varying extension from barrel rear end. When the carrier is designed to localize containers in the device housing with an for all containers common initial position of the container fronts relative the housing, a well-defined penetration action is achieved with a common penetration stroke length, again without any adaptive measure required from the user, and facilitate autopenetration and autoreturn feature in the device. In spite of any container rear end positioning variations, common penetration and injection mechanisms can be used, even with standard start positions, due to the presence of a damper, in the sense of the invention to be further explained. The damper acts to absorb otherwise destructive energy and serves to allow a broad force repertoire for the device, yet may be designed for controlled and unified delivery rates. The flexibility provided makes these features highly compatible with all basic autoinjector designs mentioned in the introduction overview and in particular force application to sensitive container barrels in a penetration step is allowed. Sequencing of autopenetration and autoinjection steps is facilitated by common start positions made possible and release of an autoreturn step is facilitated by a common piston end point, as described, or by utilization of a force, rather than location, dependent release condition, made possible by the characteristics of damped drives.

Further objects and advantages of the invention will be evident from the detailed description hereinbelow.

DETAILED DESCRIPTION

In the absence of explicit statements to the contrary, as used herein expressions like "comprising", "including", "having", "with" and similar terminology shall not be understood to be exclusively restricted to recited element but shall be understood to allow for the presence of further elements as well and shall be understood to cover any element in integral, subdivided or aggregate forms. Similarly, expressions like "connected", "attached", "arranged", "applied", "between" and similar terminology shall not be understood to cover exclusively direct contact between the recited elements but shall be understood to allow for the presence of one or several intervening elements or structures. The same applies for similar expressions when used for description of forces and actions.

The containers usable in the present autoinjector shall be understood in broad terms and can generally be said to include a barrel having a front part and a rear part defining a general axis, an outlet for the preparation, typically comprising a liquid in broad sense, arranged at the front part and at least one movable wall arranged at the rear part, a displacement of which wall causes the preparation to be moved towards or expelled through the outlet. Positional and directional statements for both the container and the autoinjector, such as "axial", "front" and "rear", shall be understood with reference to the abovesaid parts of the container. Barrel shape and movable wall have to be mutually adapted. The barrel may have a substantially constant internal cross-section, with a similarly constant barrel axis, between front and rear parts giving a generally tube-shaped barrel, and most preferably the cross-section is of the common circular type giving a substantially cylindrical barrel. The movable wall is then preferably a substantially shape-permanent, although possibly elastic, body sealingly adapted to the internal barrel surface and preferably of the piston type. At the front end of the barrel a needle, cannula or a similar penetration device is arranged and the invention is preferably used with containers wherein the needle axis is substantially parallel with barrel axis, and most preferably concentric therewith, resulting in that the penetration and the injection movements are substantially parallel. Within these limits and preferences a broad range of containers can be used with the present autoinjector device, such as ampoules, cartridges, carpoules and syringes. The container need not have a separate plunger, in which case the autoinjector mechanism can act more or less directly on the container piston, although it is often preferred that the container has a plunger, in the sense of a part protruding from barrel rear end, on which the autoinjection mechanism can act for movement of the piston, since many standardized devices are so designed and which facilitates mechanism access. The autoinjector can with preference be used with standard container types, e.g. as defined in DIN and ISO standards and exemplified with "Hypak" type syringes. Also usable are dual or multi chamber container types, known e.g. for preparations demanding a mixing of two or more components or precursors before administration. The components are kept separated by one or more intermediate walls of different known designs, which walls divide the barrel into several chambers, sometimes placed parallel along cartridge axis but most commonly in stacked relationship along the axis. Unification of the components may take place by breaking, penetrating or opening a valve construction in the intermediate walls. In another known design the intermediate wall or walls are of the plunger type and flow communication between the chambers is accomplished by moving the plunger to a by-pass section where the interior wall has one or several enlarged sections or repeated circumferential grooves and lands in a manner allowing by-flow of rear chamber content into front chamber at displacement of the rear movable wall. The chambers may contain gas, liquid or solids. Generally at least one liquid is present. Most commonly in pharmaceutical applications only two chambers are present and typically contains one liquid and one solid, the latter being dissolved and reconstituted during the mixing operation. For these types of containers it is preferred that the mixing or reconstitution step has already taken place when the container is placed in the autoinjector.

The autoinjector device comprises a housing, which shall be understood in broad sense and basically as a point of reference for positional and directional statements for other parts and components. It is preferred, however, that the housing also actually enclose at least the mechanisms of the device and leave exposed mainly the parts that should be accessible to the user, such as arming, triggering and cocking controls. The container can be attached to the housing in such a manner that it remains exposed, although it is preferred that the housing also confines the container, preferably also the needle until penetration is initiated. Replacement of containers may be facilitated by any known separation or openable arrangement, e.g. threaded or hinged parts, although a preferred and convenient arrangement is to provide an openable closure on the side of the autoinjector front part, allowing lateral insertion of the cartridge by a roughly radial movement in relation to container axis.

The autoinjector further comprises a container carrier, having the dual purpose of receiving and holding the various containers in defined relationship to the housing and mechanisms and being axially movable in relation to the housing, for penetration purposes, between a rear position and a front position, movement between which positions is used for penetration. The distance traveled between the positions should correspond at least to the desired penetration depth and, when the needle is hidden within the housing before the penetration step, the distance needed for internal travel to expose the needle tip. The carrier should be able to accommodate at least two and preferably several container types of different width and/or length, preferably also differences in other respects earlier mentioned, i.e. the carrier should have features allowing releasable fixation and axial displacement thereof without individual inserts or other auxiliary devices. This can be accomplished by use of at least one flexible or spring biased member arranged to press the container radially against at least one rigid surface, preferably in the from of a trough allowing acceptance of different widths, e.g. by having an axially constant V-shaped profile. It is also preferred that the container is axially fixed in the carrier, at least against forward movements, e.g. by use of a stop surface, and preferably so that all container types are similarly held, for example behind container rear end fingergrips but preferably in front of barrel front end, giving the advantages outlined.

The autoinjector shall contain at least an autopenetration mechanism and an autoinjection mechanism and preferably also contains an autoreturn mechanism to be further described below. The mechanisms may be of any known types mentioned in the introduction but, for reasons given, is preferably of the type applying penetration force to the barrel or the container carrier, rather than the piston or plunger. The autoinjection mechanism comprises at least a penetration head, arranged for contact with the barrel or carrier in the penetration step and possibly also maintained under the injection step, and a penetration drive able to apply force between the housing and the penetration head. The penetration head can be a larger structure or aggregate accessible for the autoinjection mechanism or control system. Similarly the autoinjection mechanism comprises at least an injection head, arranged for contact with the container piston or plunger in the injection step, and an injection drive able to apply force between the housing and the injection head, between the penetration head and the injection head or between the carrier and the injection head. The distinction herein between the penetration head and the injection head shall not exclude the use of a common head acting as both penetration head and injection head, in which case the common head should first act on the barrel or carrier and then on the piston or plunger. It is preferred, however, to use at least partially different head structures, among others facilitating adaptations for their respective purposes and their proper positioning for all container variations. A common drive can be used for the single or dual head alternatives, which is possible according to the invention and which gives the simplest device construction. It is preferred to use different drives, though, in which case the penetration drive is preferably made substantially weaker than the injection drive, as penetration normally give little resistance, which makes it possible to avoid the initially mentioned vibration and rebound effects during the relatively large penetration stroke while maintaining a strong injection drive.

A control mechanism for sequencing the penetration and injection steps may comprise a releasable penetration lock arranged for holding the penetration head relative the housing and a releasable injection lock for holding the injection head either relative the housing, which allows for entirely independent injection start, or preferably relative the penetration head or carrier, which allows for an aggregate of parts, including the injection head and preferably also the injection drive, to move forwards during penetration, thereby limiting the dead run for the latter and adapting it to the container rear end sensed by the penetration head. The locks are arranged to hold the heads in predetermined rear cocked positions, to which positions it should be possible to move the heads by an externally accessible handle or similar control. It is preferred that in the cocked positions there is a space between the penetration head and the barrel or carrier and a space between the injection head and the piston or plunger respectively, thereby allowing for containers of different lengths or filling degrees. When the injection head is locked relative the penetration head it is similarly preferred that a space remains between the injection head and the piston or plunger after the penetration stroke and before injection. The control system preferably also includes an externally accessible manual trigger arrangement at least acting to release the penetration lock. Release of the injection lock can take place simultaneously with the penetration lock, especially if the injection stroke is delayed by speed controlled to be explained, but it is safer and preferred to make the release at or close to the end of the penetration stroke, either by using the increased force sensed by the penetration head at the end of the penetration stroke, which gives the most adapted release for any container, or a specific point at the housing, which gives the overall simplest solution. When the releasable injection lock is connected, directly or indirectly, between the injection head and the penetration head or carrier as said, this can be implemented by inclusion of a structure on the housing releasing the injection lock at a predetermined axial injection enabling position for the penetration. This is possible both if separate drives are used for penetration and injection and if single drive is used if the single drive acts on the injection head.

As indicated it is preferred that the autoinjector also includes an autoreturn mechanism including a return drive arrange to apply force between the housing and the container barrel or carrier for movement in the rearward direction. This can be done, in a manner known per se, by allowing the return drive force to give a constant bias rearwardly, such as by a counterspring, and using a return drive force weaker than the force provided by the penetration force. The control system may then comprise an autoreturn enabling mechanism disengaging the container and carrier from the autoinjection force and the autopenetration force, thereby freeing the container for rearward motion. The penetration and injection mechanisms should allow for unobstructed return, e.g. by being laterally displaced or by having cavities for reception of the container rear parts. For simplest design the autoreturn enabling mechanism may include a release structure, arranged to enable the disengagement, with predetermined axial location in relation to the container front. Alternatively and preferably the autoreturn enabling mechanism may be designed to react on the increased force resulting from the piston reaching and being stopped at the container bottom end, which secures complete emptying and squeezing out of container content and furthermore is highly independent of container type. In one embodiment this is achieved in that the autoinjection mechanism comprises an injection conveyor, that the injection drive acts between the injection head and the injection conveyor, that the injector head is connected to the penetration head via the injection conveyor, that the injection conveyor is axially movable with respect to the penetration head, that a counterforce, being weaker than the force of the injection drive, is arranged between the injection conveyor and the penetration head and that the autoreturn enabling mechanism includes release mechanism acting on a relative movement between injection conveyor and penetration head. Optionally the force based release can be enabled only short before injection completion and be disabled during the main part of the injector head movement not to be activated by abnormal force increases, e.g. due to flow blockages or container malfunction.

The various drives described may utilize stored energy in any known form, such as electrical, gas pressure or gas releasing, or preferably mechanical, the latter preferably in the form of elastic members such as springs. The stored energy can be transmitted to the force stated via corresponding conventional transmission means, e.g. electromechanical, such as electric motors or solenoids, hydraulic, pneumatic etc. system but preferably mechanical springs are utilized.

According to the invention at least one damper shall be present, which damper shall be able to absorb work, i.e. force times way, energy forms. The damper may absorb the energy mainly reversibly in elastic form, utilizing well known components for this purpose, such as elastomeric materials, e.g. rubbers or mechanical springs. For certain purposes it is preferred to use in-elastic damper types, i.e. absorbing energy mainly irreversibly and under heat generation, utilizing either materials being permanently deformed but preferably, for repeated use, viscous dampers in the meaning of having a fluid, gas or preferably a liquid, arranged to pass a flow restriction or between shear surfaces during displacement of its parts. Viscous dampers, or dash pots, are well known components as such and may take a variety of forms, e.g. axial, as exemplified by piston/cylinder types in which the fluid passes constrictions in or around the piston or in controlled shunt, or rotational, as exemplified by impellers rotating in a fluid under generation of shear forces. Although some of the abovesaid dampers, e.g. elasticly or inelastically deformable materials, are able to absorb energy in more than one direction, it is generally sufficient for the present purposes that the damper can absorb energy in one direction. Still a transmission may be needed, e.g. to transform a linear movement in the autoinjector into a circular movement in rotational viscous dampers, to permit space-conserving repositioning of the damper or to allow for a force modifying lever arrangement. Generally it is preferred to arrange the damper in parallel with the linear motion to be damped for simplest overall layout. Preferably viscous dampers can be arranged to be active only in one direction, preferably the injection or penetration directions, but not in the reverse, e.g. to allow unobstructed cocking or the device, which can be accomplished in well known manners, e.g. by providing a releasable connection of the damper or preferably by making the flow restriction according to one-way valve principles.

The damper can be arranged for energy absorption from the autopenetration movement, for which purpose the damper should yield under a pressure weaker than the force provided by the autopenetration drive but preferably be stronger than force provided by the autoreturn mechanism when present. It follows that, although for example a return counterspring in a autoreturn mechanism may act as a damper, for the present purposes the damper is separate and in addition thereto. Preferably the damper is arranged to absorb energy at impact forces between the autopenetration head and the container barrel or carrier, which impact forces may occur at the forward extreme for the penetration movement when the container/carrier aggregate stops and often also in the beginning of the penetration movement at the attack of the penetration head against barrel or carrier. The damper can be arranged at or on the barrel or carrier but it is preferred to include the damper in the autopenetration mechanism, anywhere between the housing and the penetration head front. The penetration head as such can be made wholly or partially resilient for best overall simplicity but it is preferred to subdivide the head on at least two parts and arrange the damper therebetween for best control. It is further preferred to utilize the movement under damper yield as a confirmation of penetration movement completion, e.g. for release of the autoinjection phase. It is generally preferred that needle penetration takes place rapidly, as this limits the pain sensation and as there are no advantages in extending this act. Accordingly it is generally preferred to arrange the damper to be active only over a part, and preferably only a minor part, of autopenetration movement, preferably the last part thereof, possibly also the initial part, while leaving the major part of the movement undamped. Since needle penetration normally requires only small forces, furthermore fairly independent of syringe types, the damping requirements are small and can sometimes be omitted entirely when the force of the autopenetration mechanism can be adapted to the penetration purpose solely, which is the case especially when this drive is independent of the autoinjection mechanism drive system.

Most preferably a damper is arranged for energy absorption from the autoinjection movement, for which purpose the damper should yield under a pressure weaker than the force provided by the autoinjection drive. A damper may here be included for similar impact preventing purposes as described above for the autopenetration phase and similar considerations then apply, e.g. be active only under the relevant part of the movement, typically under the injection head attack phase against piston or plunger. During autoinjection, however, it is preferred that a damper is additionally or alternatively provided for the purpose of controlling injection movement speed and force in order to make the autoinjection phase usable for a broad range of forces with maintained uniform movements speeds, as described in the introduction. Typical injection times are between 0.5 to 30 seconds and preferably between 1 and 10 seconds. Accordingly damping should be active during a major part of the autoinjection movement, preferably over substantially the whole injection stroke and preferably also before injection head contact with plunger or piston, the latter additionally acting to reduce attack and dead run problems and allowing for use of different sized containers. The drive force can and should be selected strong enough, and preferably more strong than that required, for the most demanding force requirement of all container alternatives designed for, as the damper will limit speed and force sensed by the container to acceptable levels also in less demanding situations. It is preferred that the driver and damper in combination gives the injection head a substantially stable speed already in idle run, i.e. without container present, and most preferably roughly that of acceptable maximum piston or plunger speeds. It is further preferred that during the injection movement the resistance in the damper is higher than the resistance, such as flow and friction resistance, in the container. For these purposes viscous dampers, as described, are preferred e.g. for allowing long damped movements and for best damping characteristics. As indicated the damper should preferably be arranged to be active during the actual injection stroke as well as during any further initial length necessary for allowing the injection head to start from a for all container types contemplated common start position for the injection phase. Any additional movement over that need not be damped, e.g. any movement the injection head makes earlier during the autopenetration phase, for example when in a preferred way moving together with the penetration head during the autopenetration phase. The latter can be accomplished if the damper is connected between the autopenetration head and the autoinjection head, whereby damper movement will only take place when the injection head moves relative the penetration head, normally after completed penetration. Similarly, any injection head movement after completed injection need not, and preferably is not damped, e.g. any movement during the autoreturn phase, which, however, is automatically obtained in the preferred arrangement mentioned that during autoreturn the carrier is simple released from the heads and accordingly also under inactivated damper. In any case the preferred connection principle is to install the damper at least partially in parallel with the injection mechanism, so that during the damped movement the damper parts necessarily and positively moves when the injection head moves.

A further advantage of the damped autoinjection mechanism as described may be obtained in connection with an autoreturn mechanism, which as said needs that the control system provides a release of the carrier at the end of the injection phase. As generally described earlier, release can be controlled by the arrival of injection head, piston or plunger at a certain location corresponding to the piston arriving at the barrel front end and here the damper acts to give a cautious release highly independent of variations in container injection resistance. It is preferred to use a damper in connection with the alternative mentioned in which the release is controlled by an increased force generated at the piston contact with container front. Here a damper, especially a viscous damper, will give full control over the force increase as during movement of the injection head the damper secures a predetermined reduction of the injection drive nominal force through energy consumption whereas at stop of the movement the damper is inactivated and said full nominal force is restored between drive and plunger head. Similarly at gradual retardation of the injection head the force increase will be correspondingly gradual. All in all a substantial force difference will be available for use by the control system in performing release of the autoreturn function. When, in a preferred manner this principle is applied in the conveyor type arrangement included in the autoinjection mechanism, as earlier described, the gradual force buildup and substantial force difference provided by the damper allow i. a. a long conveyor movement and significant force difference between injection drive force and conveyor counterforce, all serving to make the autoreturn release reliable, rugged and adaptive.

Further details of the invention will be eident form the description of specific embodiments in relation to the drawings.

DESCRIPTION OF DRAWINGS

Figure 1A:
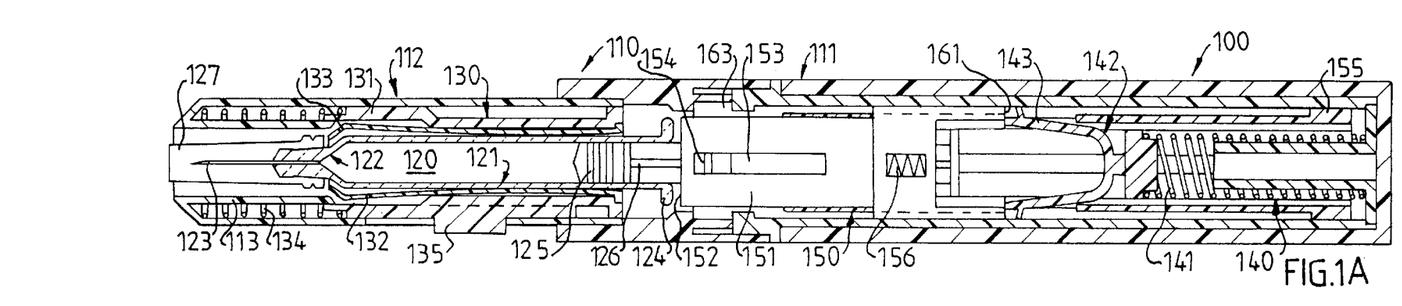
FIGS. 1A to 1D show schematically in section four operational stages of a first embodiment of an autoinjector having a common drive for autopenetration and autoinjection and having elastic dampers.
Figure 1B:
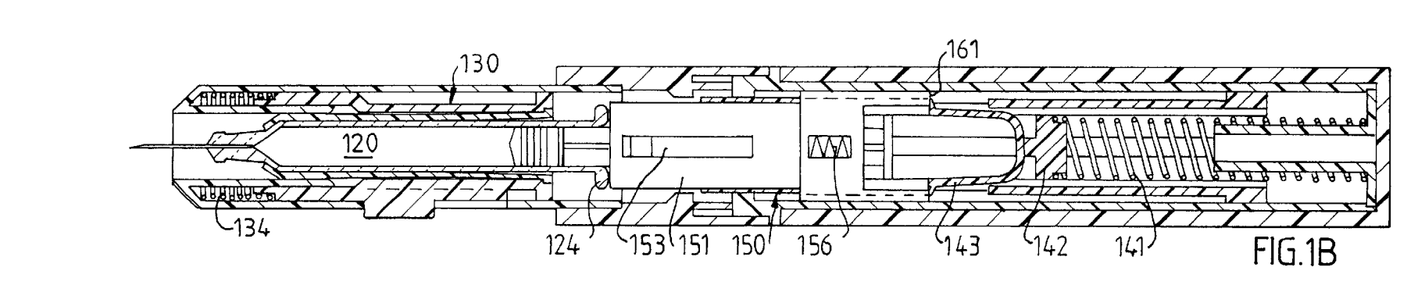
Figure 1C:
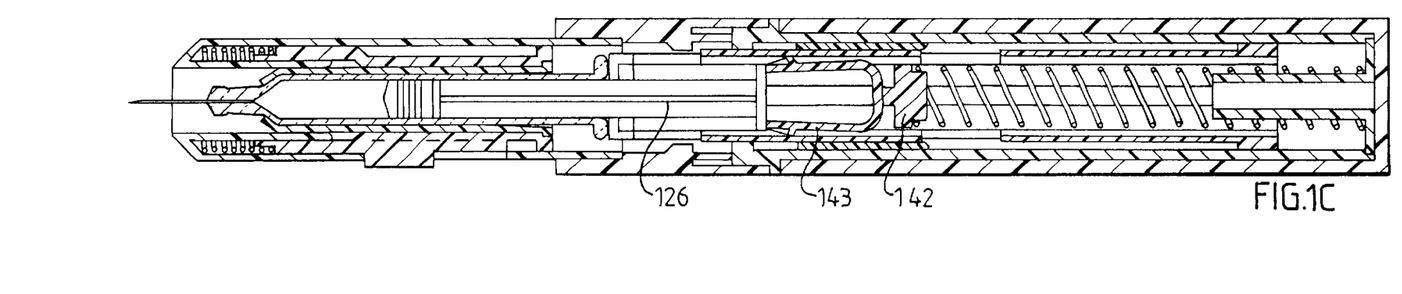
Figure 1D:
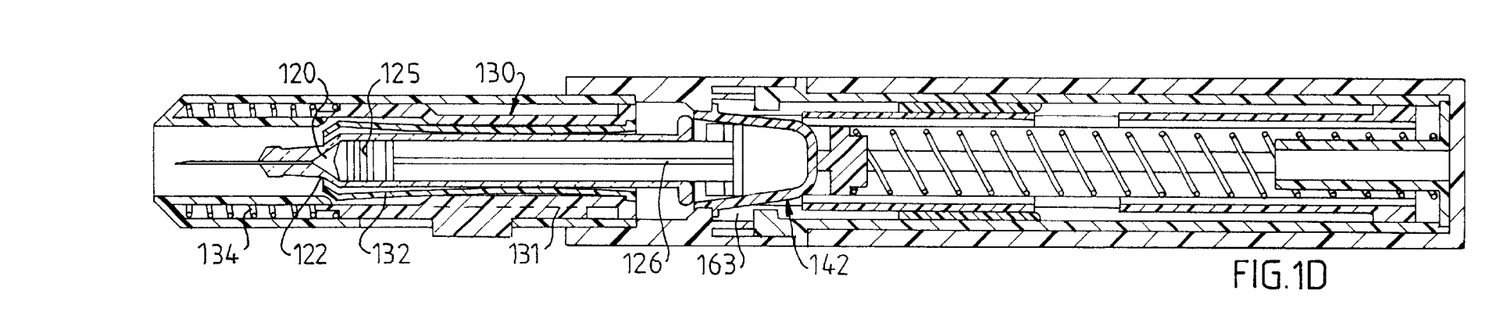

FIGS. 1A to 1D show schematically in section four operational stages of a first embodiment of an autoinjector having a common drive for autopenetration and autoinjection and having elastic dampers. In FIG. 1A the autoinjector is in an initial cocked position before triggering. FIG. 1B shows the device after the autopenetration step, bringing the needle to an exposed position. FIG. 1C shows the device during the injection phase when the piston has been brought to an intermediate position within the container. FIG. 1D shows the device after that the autoreturn mechanism has moved the syringe back into a needle-hidden position. The autoinjector, generally designated 100, comprises a housing 110, divided into a rear housing part 111, essentially confining the mechanism parts, and a front housing part 112, essentially confining the container parts. The housing parts are separable, allowing insertion and replacement of containers, generally designated 120, and comprising a barrel 121, a front part 122 with attached needle 123, a rear fingergrip part 124 and a piston 125 inserted in the barrel onto which piston a plunger 126 acts. A removable needle cover 127 initially protects the needle. The front housing part 112 also contains a container carrier, generally designated 130, comprising an axially movable seat 131 for reception of containers, a flexible insert 132 allowing accommodation of containers of different diameters, which insert has inwardly tapering surfaces 133 arranged to restrain container front 122 from forward movements relative the carrier and being pushed by inner sleeve structure 113 on the front housing part to an engaging position at least when the carrier is in the needle exposing position. A return spring 134 is arranged between the front housing part 112 front end and carrier 130 for movement of the carrier in the rearward direction. The seat has a knob 135 extending laterally through a slit in the hosing front part to an externally accessible position for manual movement of the carrier forwards against the bias of the return spring, e.g. for removal or attachment of needle cover 127. The rear housing part 111 comprises most of the device mechanisms. A common drive system includes a spring 141 acting as both as penetration drive and injection drive. The spring acts between housing rear end and an injection head 142 in resilient material giving impact damping and having a generally U-shaped form with legs 143 able to flex laterally in and out and forming a cavity therebetween able to receive, when in an out-flexed position, the plunger 126 rear part during the autoreturn phase. A penetration head aggregate, generally designated 150, comprises a front generally sleeve-shaped syringe plunger part 151, having a front surface 152 arranged for contact with barrel rear end or fingergrip 124, and a rear plunger guide 153, having a front end 154 extending into the sleeve-like syringe plunger part 151 and a rear end 155 extending well behind the syringe plunger 151. Between the syringe plunger 151 and the plunger guide 153 a compression damper spring 156 is arranged in slots, biasing the plunger guide 153 towards a rear position relative the syringe plunger 151. The control system can be said to include an externally accessible releasable lock (not shown) for holding the penetration head in the rear cocked position, and thereby also holding the injection head 142 in its cocked position to be explained, thereby serving both as penetration lock and injection lock. The control system further comprises structures, for sequencing the operation, by flexing the injector head legs 143. A first such structure comprises tapering surfaces 161 at the syringe plunger 151 rear end, arranged to compress the legs 143 from an intermediate position (shown in FIG. 1A), in which the legs act on the plunger guide 153, to a narrow position (shown in FIGS. 1B and 1C), in which the legs are freed to land on syringe piston 126 and maintained compressed by channel 162 provided by the plunger guide 153. The tapering surfaces become active for compression of the legs when the plunger guide moves forward relative the syringe plunger against the force of the damper spring, which is weaker than the drive spring 141. A second control structure comprises an expansion cavity 163 adapted to allow expansion of the legs 143, at a position corresponding to plunger 126 final position at empty syringe, to an expanded position (shown in FIG. 1D) allowing the plunger 126 to move into the space between legs 143 under the action of return spring 134 to a needle-hidden syringe position.

In FIG. 1A penetration head 150 is held in a rear cocked position at a short distance from syringe barrel end or fingergrip 124. The injection head 142 is also held in a rear position since legs 143 rests in a slot on plunger guide 153. The drive spring 141 is compressed. The container 120 is pressed to a rear needle-hidden position by return spring 134. In FIG. 1B a trigger (not shown) has been released and drive spring 141 has acted on injection head 142, which in turn has acted on plunger guide 153 to move syringe plunger 151, into contact with container barrel or fingergrip 124, thereby moving the container and carrier 130 into a needle-exposed position. At the end of this penetration movement the container and carrier have stopped together with syringe plunger 151 but the plunger guide 153 has continued its forward movement against the weaker force of damping spring 156, the relative movement between which parts has made the tapering surface 161 cause a compression of legs 143 and the injection head has landed on container plunger 126. In FIG. 1C (showing the penetration aggregate in section rather than view) the injection head 142 has moved container plunger 126 a certain distance under expulsion of container content and with legs 143 in maintained compressed condition by channel surfaces 162. In FIG. 1D the piston 125 has arrived at container front part 122, injection head legs 143 have arrived at expansion cavity 163, the legs have expanded away from contact with the plunger 126 and return spring 134 has moved container 120 and carrier 130 to the initial rear needle-hidden position under partial reception of the exposed rear plunger 126 part in the space of the U-shaped injection head 142.

Figure 2A:
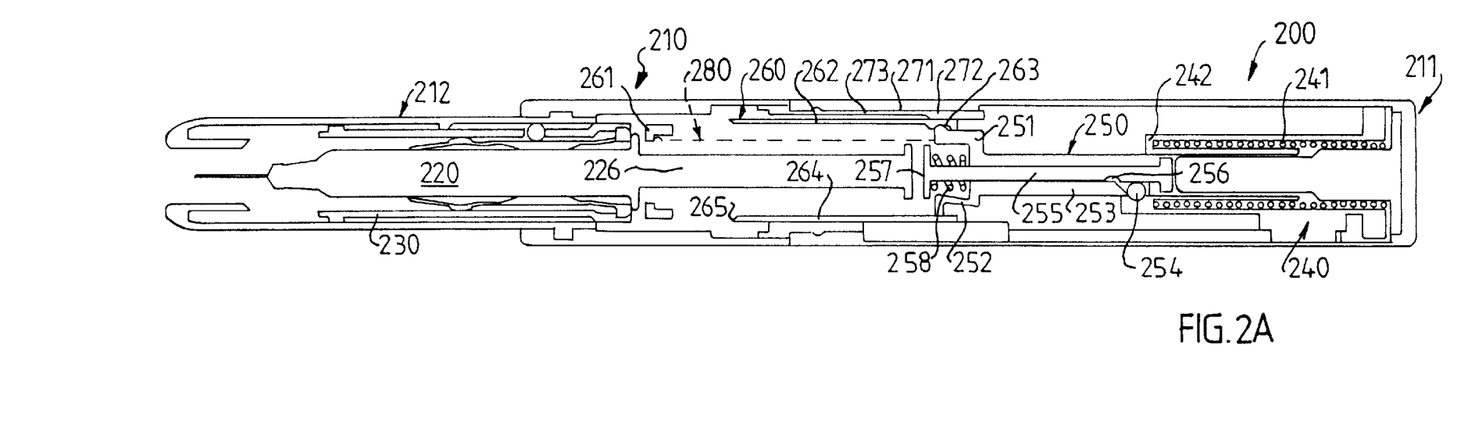
FIGS. 2A to 2G show schematically in section seven operational stages of a second embodiment of an autoinjector having a common drive for autopenetration and autoinjection and being modified for a viscous damper.
Figure 2B:
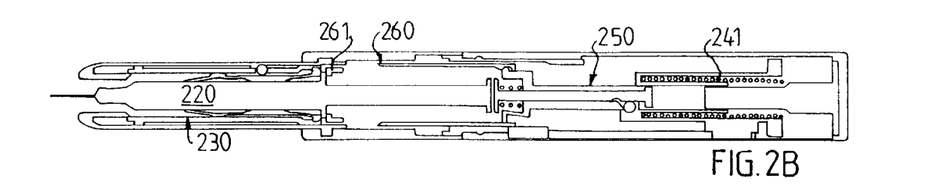
Figure 2C:
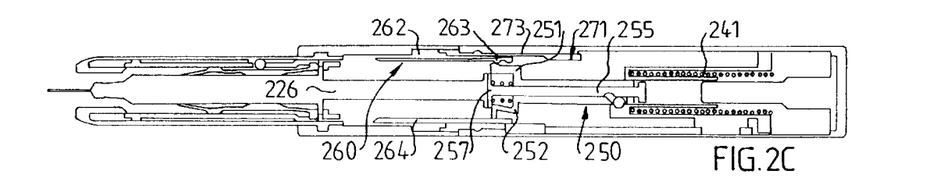
Figure 2D:
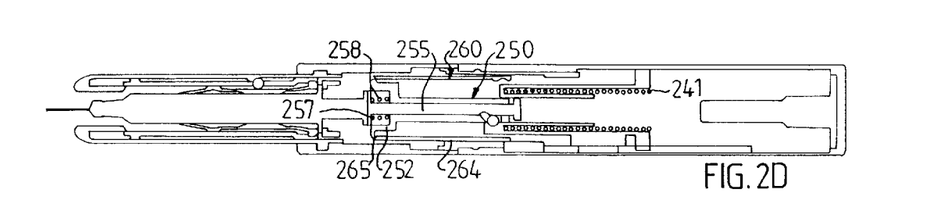
Figure 2E:
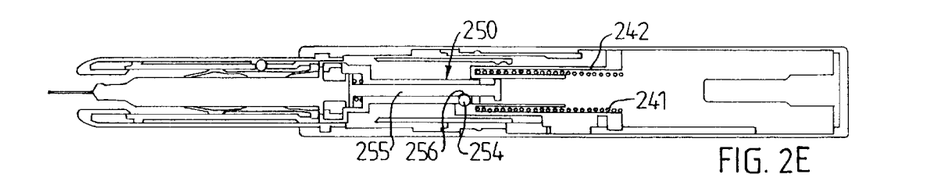
Figure 2F:
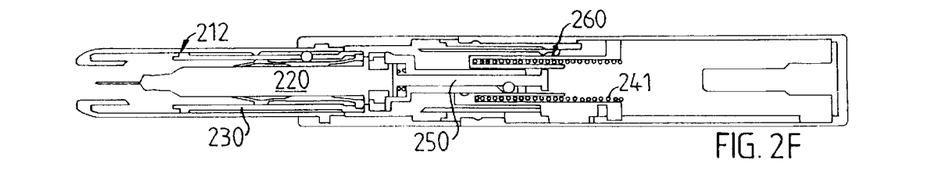
Figure 2G:
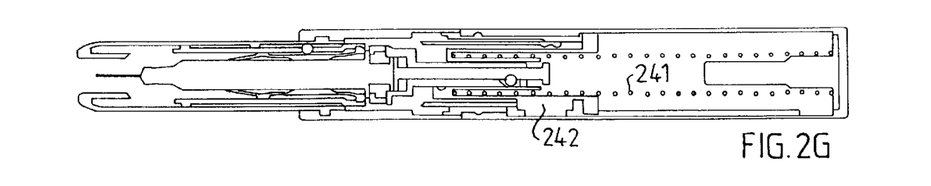

FIGS. 2A to 2G show schematically in section seven operational stages of a second embodiment of an autoinjector having a common drive for autopenetration and autoinjection and being modified for a viscous damper. In FIG. 2A the autoinjector is in an initial cocked position before triggering. FIG. 2B shows the device after the autopenetration step, bringing the needle to an exposed position. FIG. 2C shows the device having just started the injection phase when the injection head and piston has come into contact. FIG. 2D shows the device at end of the injection phase at initiation of autoreturn phase. FIG. 2E shows the device when release of a ball lock has freed the injection head from the injection drive. FIG. 2F shows the device after that the autoreturn mechanism has moved the syringe back into a needle-hidden position together with the injection head. FIG. 2G shows the device when the main drive spring has been fully extended. The embodiment of FIG. 2 has many features in common with that of FIG. 1 and shall be describe in detail only with respect to features principally deviating therefrom. Referring first to FIG. 2A the autoinjector 200 comprises a housing 210 having a rear part 211 and a front part 212 separable for insertion of a container 220, with plunger 226, in a movable carrier 230, biased rearwards by a return spring (not shown). The rear housing part 211 comprises a drive system 240, acting both as penetration drive and injection drive, having a main compression spring 241, housed within a drive sleeve 242, acting on a injection head aggregate, generally designated 250. The aggregate 250 comprises a U-shaped front of an upper rigid leg 251 and a lower flexible leg 252. A tube 253 extends rearwards to the drive and is attached to the drive sleeve 242 with a ball lock, comprising a ball 254 and a control pin 255, with a ball releasing cavity 256 and a front flange 257. A ball lock spring 258 gives the control pin a forward, locked, bias versus the tube 253. A penetration head aggregate, generally designated 260, comprises front surfaces 261, arranged for contact with container barrel or fingergrip, which surfaces are connected to a transport guide 262 having a catch 263, for reception of rigid leg 251, at a resilient part of the transport guide, a guide rail 264, arranged for keeping the flexible leg 252 in an in-flexed state, the guide rail 264 having a forward end 265, arranged to allow flexible leg 252 to flex out. A further control structure comprises a cam surface 271 fixed with respect to the housing and having a thick rear part 272, adapted to keep catch 263 of the transport guide 262 pressed against the rigid leg 251 in engaged relationship, and a thin front part 273, adapted to allow the catch 263 to flex out for disengagement of rigid leg 251. Although not shown in detail the device is adapted for use with a viscous damper, arranged between the penetration head 260 and the injection head 250 to be active only during relative movements therebetween. Dotted line 280 illustrates schematically a linear damper, such as a piston/cylinder oil damper, attached between penetration head 260 front surfaces 261 and injection head 250 rigid leg 251, for parallel axial movement of damper and injection movement.

In FIG. 2A penetration head 260 is held in a rear cocked position by a releasable trigger mechanism (not shown). The injection head 250 is also held in a rear position since rigid leg 251 is engaged in the catch 263. The drive spring 141 is compressed and acts on the injection head as the control pin 255 is in its locked state. The container 220 is pressed to a rear needle-hidden position by the return spring. In FIG. 2B a trigger has been released and drive spring 241 has acted on injection head 250, which in turn has acted on penetration head 260 to move surfaces 261 into contact with container barrel or fingergrip, thereby moving the container 220 and carrier 230 into a needle exposed position. During this movement the viscous damper 280 is inactive as the penetration head 260 and injection head 250 moves together. In FIG. 2C the catch 263 section of the transportation guide 262 is at the thin part 273 of cam surface 271 and has flexed out, thereby freeing rigid leg 251 from the catch 263 and allowing the injection head 250 for movement independent of the penetration head 260, which is now decoupled form the drive spring 241. Viscous damper 280 is now active and serve to retard injection head 250 forward movement during the injection movement. In the figure the independent movability has also resulted in that the flange portion 257 of control pin 255 has come into contact with container plunger 226 for injection. Flexible leg 252 is still maintained in-flexed by guide rail 264 of transportation guide 262, thereby preventing the control pin 255 from moving rearwards. In FIG. 2D injection has proceeded to end and the injection head 250 is in a forward extreme position with respect to the housing and the penetration head 260. In this situation the flexible leg 252 has reached the end 265 of guide rail 264 and has flexed out, thereby freeing the flange 257 of control pin 255 for rearward movement against ball lock spring 258, which is weaker than drive spring 241. In FIG. 2E the control pin 255 has moved rearwards with respect to the injection head 250 (which has moved a bit more forwards), placing ball releasing cavity 256 at ball 254, thereby releasing the injection head from the drive sleeve 242, resulting in disengagement from the drive spring 241. In FIG. 2F a return spring at the front of housing front part 212 has pushed the container 220 and container carrier 230 back into the rear needle-hidden position, unrestricted of the drive spring 241 since the injection head 250 is decoupled therefrom and moves with the container and as the penetration head has been decoupled earlier. This movement is also unaffected of the viscous damper 280 as both penetration head 260 and injection head 250 moves in concert. In FIG. 2G the drive spring 241 and drive sleeve 242 have continued their decoupled movement to a forward extreme position in which the drive spring 241 is fully extended (partial extensions not shown in earlier Figures).

Figure 3A:
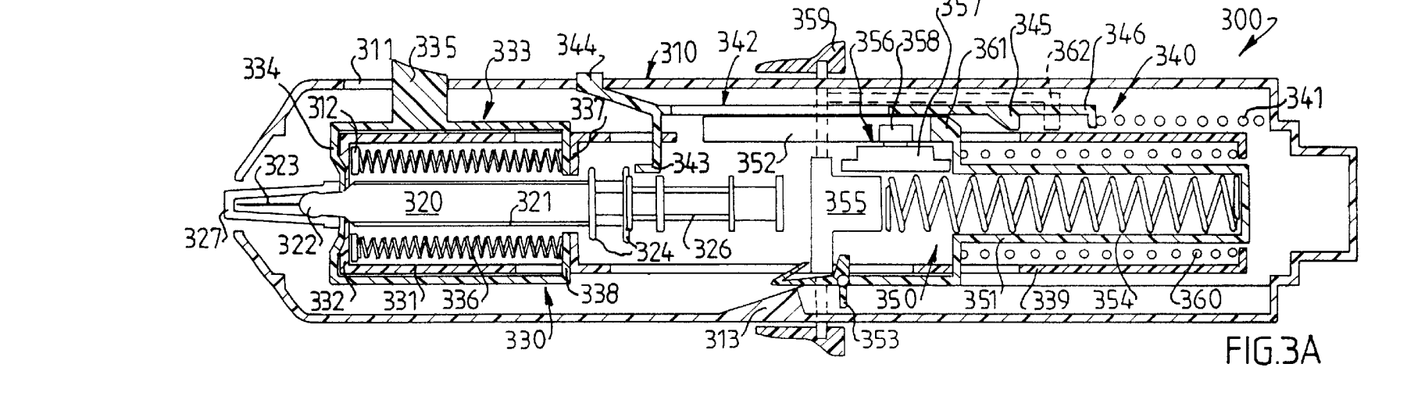
FIG. 3A to 3J show schematically in section ten operational stages of a third embodiment of an autoinjector having a separate drives for autopenetration and autoinjection and having a viscous damper being arranged for force determined autoreturn release.
Figure 3B:
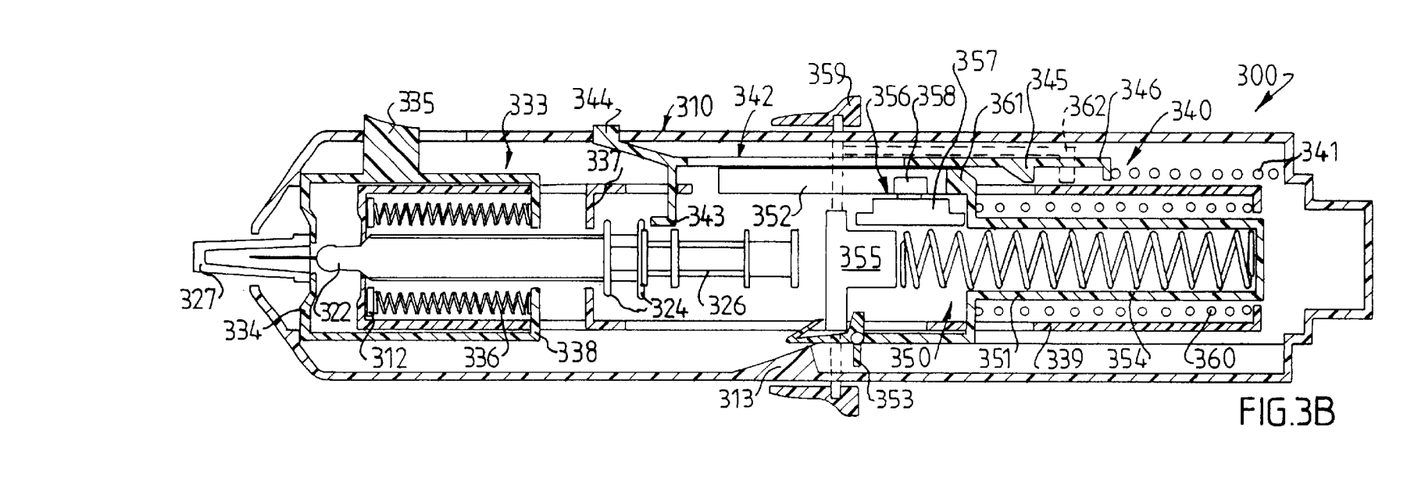
Figure 3C:
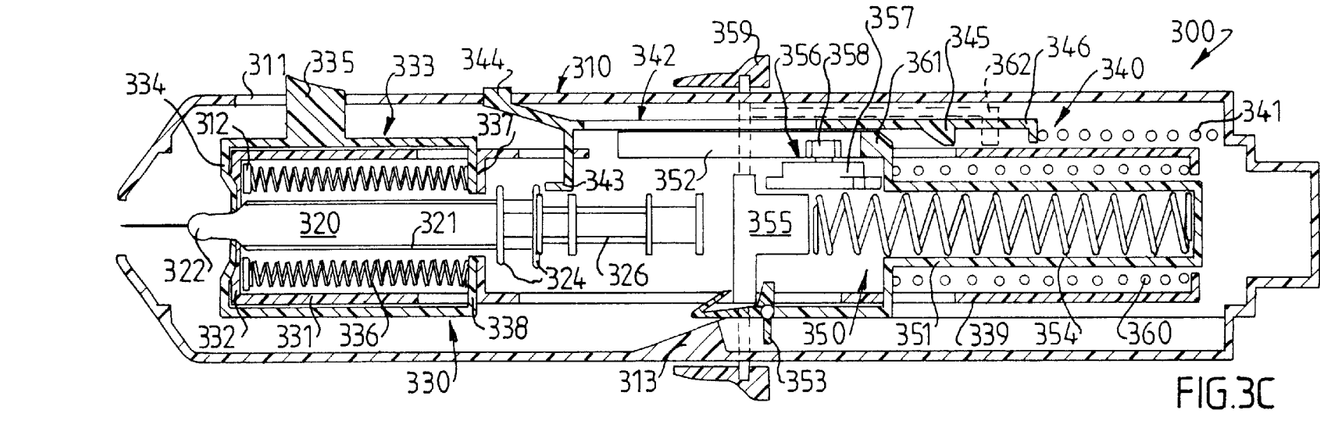
Figure 3D:
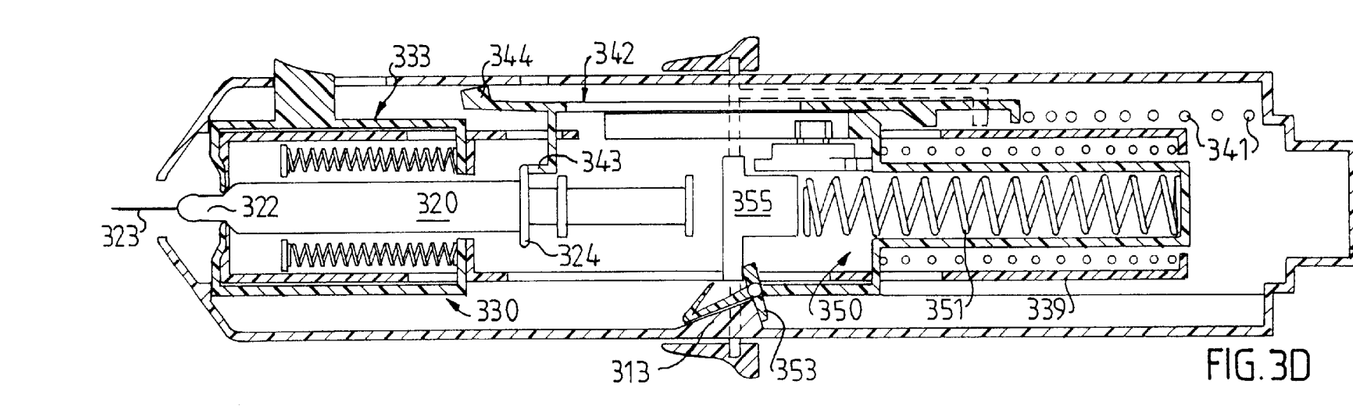
Figure 3E:
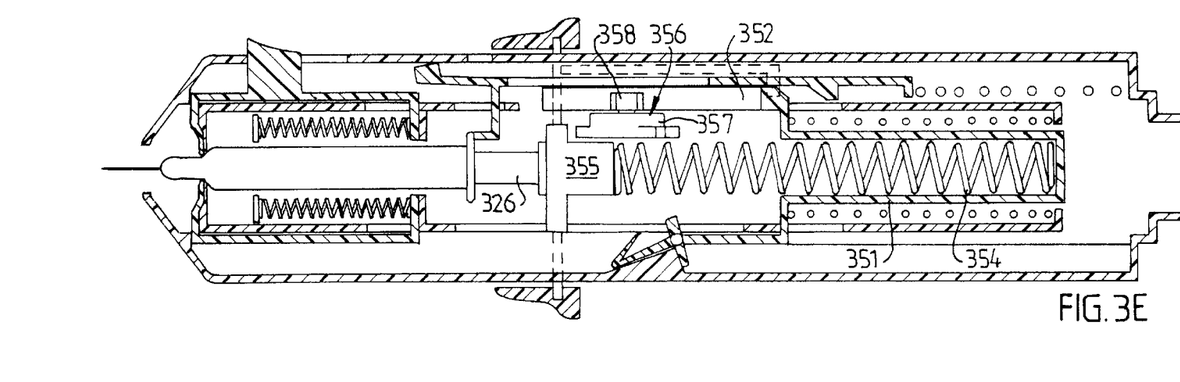
Figure 3F:
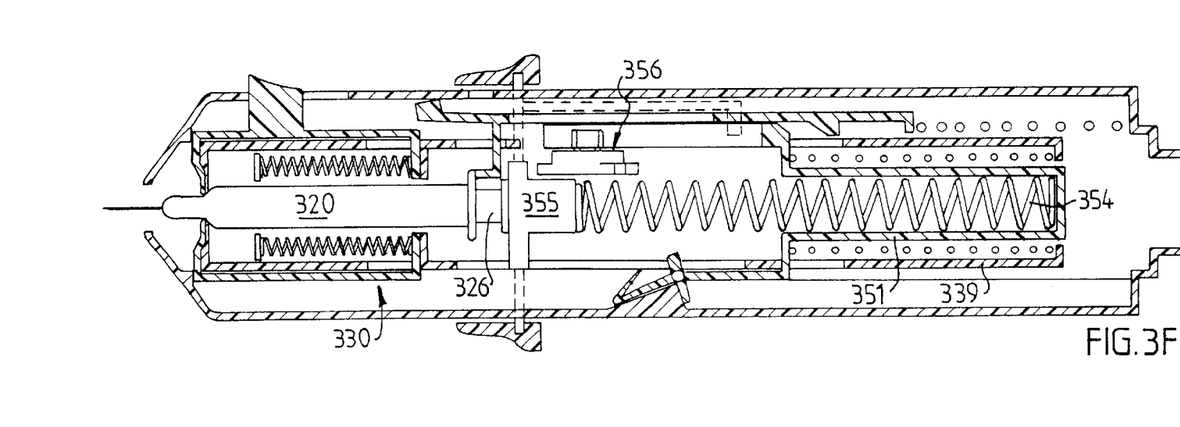
Figure 3G:
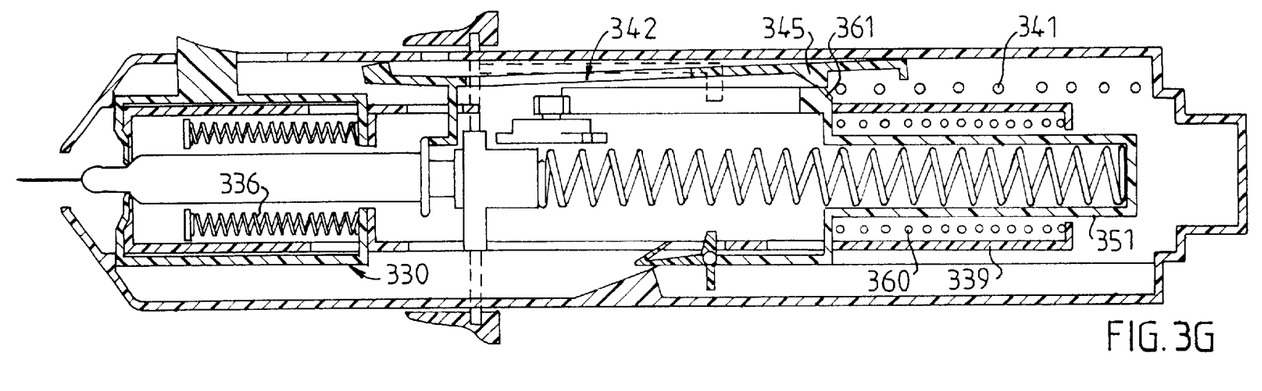
Figure 3H:
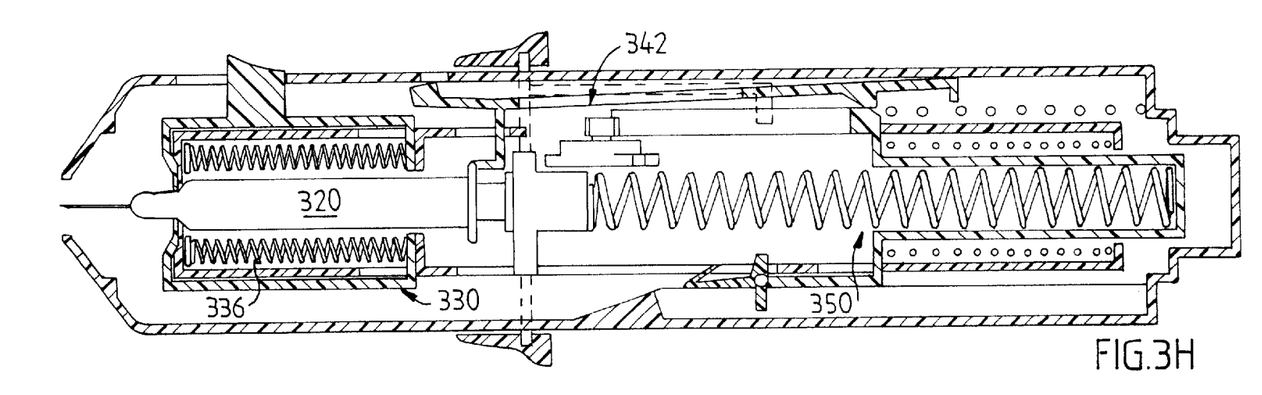
Figure 3I:
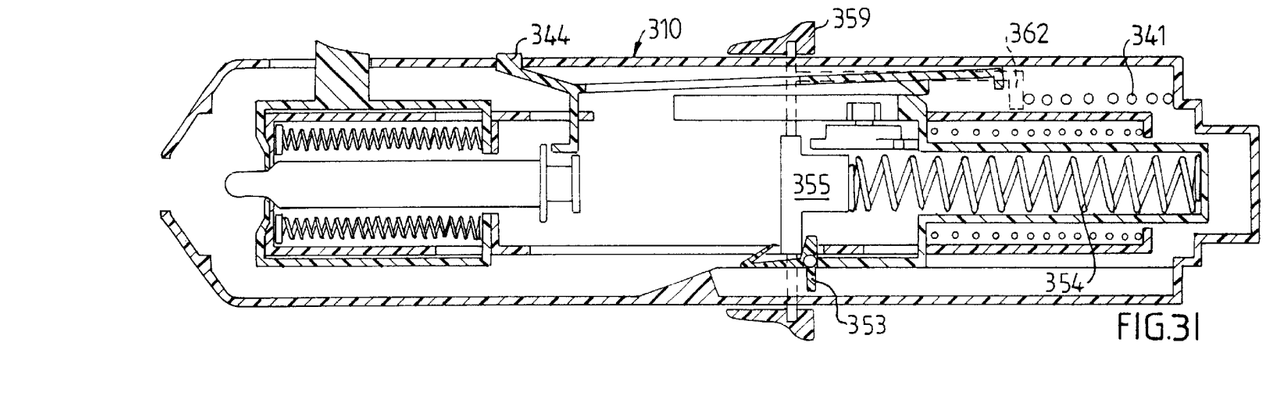

FIGS. 3A to 3J show schematically in section ten operational stages of a third embodiment of an autoinjector having a separate drives for autopenetration and autoinjection and having a viscous damper being arranged for force determined autoreturn release. The operational stages are shown for two syringes of both different lengths and widths, drawn in an overlapping manner in the initial Figures. In FIG. 3A the autoinjector is in an initial cocked position. In FIG. 3B the syringe and carrier have been brought forward manually for access and removal of a needle cover and in FIG. 3C the syringe is again in the rear position ready for triggering. In FIG. 3D the device has been triggered, autopenetration has taken place and the injection head is released for forward motion. FIG. 3E shows the device after partial injection of syringe content and FIG. 3F at the end of the injection stroke. In FIG. 3G the pressure increase at plunger bottoming out has caused compression of a rear counterspring used for release of the main spring. In FIG. 3H the released syringe has moved back into a needle hidden position. FIG. 3I shows the device re-cocked and FIG. 3J the device after syringe removal, ready for replacement. The autoinjector, generally designated 300, comprises a housing 310, in this embodiment an integral structure with a front closure, laterally openable for access to the carrier. The housing among others have a front slit 311 for a remover button, foundations 312 for a return spring and a control structure 313 for a release hook. The syringe type container, generally designated 320 and shown in two sizes as said, comprises barrels 321, front parts 322 with attached needle 323, rear fingergrip parts 324 and plungers 326. A removable needle cover 327 initially protects the needle. The housing 310 also contains a container carrier, generally designated 330, comprising an axially movable seat 331 for reception of containers, which seat has inwardly directed surfaces 332 arranged to restrain container front 322 from forward movements relative the carrier. Surrounding the seat 331 is a cover remover 333 having a forward restriction 334 gripping behind the needle cover 327 and being axially movable relative the carrier by manipulation of an externally accessible button 335, extending through the housing slit 311. Return springs 336 are arranged between the housing foundations 312 and rear flanges 337 on carrier 330, via rear flanges 338 on the remover 333, the return springs 336 being biased for movement of the carrier in the rearward direction. The carrier 330 extends rearwardly to form a support part 339, which support houses parts of the injection mechanism to be described. An autopenetration mechanism, generally designated 340, comprises a penetration drive spring 341 acting on a penetration head structure 342, having a contact surface 343 arranged for pushing the syringe barrel 321 or fingergrip 324 forwards. The penetration head 343 also comprises a trigger button 344 extending through the housing 310 wall and a tapering surface 345 arranged for cooperation with another structure to deflect the rear part 346 of the penetration head out of engagement with the drive spring 341. The autoinjection mechanism, generally designated 350, comprises a conveyor 351, forming a base for the injection drive, the conveyor extending forwardly into a toothed rail 352 of a length corresponding to at least the stroke length for the injection head. A head hook 353 is also arranged on the conveyor. An injection drive spring 354 acts between the conveyor 351 and an injection head 355, axially movable in relation to the conveyor and arranged for displacement of the syringe plunger 326. A rotational type dashpot damper 356 has its stator part 357 attached to the injector head 355 and its toothed rotor wheel 358 engaged with the toothed rail 352. Connected with the injection head 355 is also an externally accessible cocking handle 359 extending into a pusher 362 for the penetration drive spring 341. The conveyor 351 is arranged axially movable in relation to the carrier 330 support part 339 via a counterspring 360 between these parts, which counterspring is weaker than the injection drive spring 354 and arranged to bias the conveyor 351 forwardly with respect to the support part 339. This arrangement being part of the control system to be explained. The control system can also be said to include the housing control structure 313, arranged to tilt the head hook 353 and freeing the injection head 355 at a certain axial location for the carrier with respect to the housing, and a structure 361 on the conveyor, arranged to cooperate with the tapering surface 345 on the penetration head to disengage the latter from the penetration spring 341.

Figure 3J:
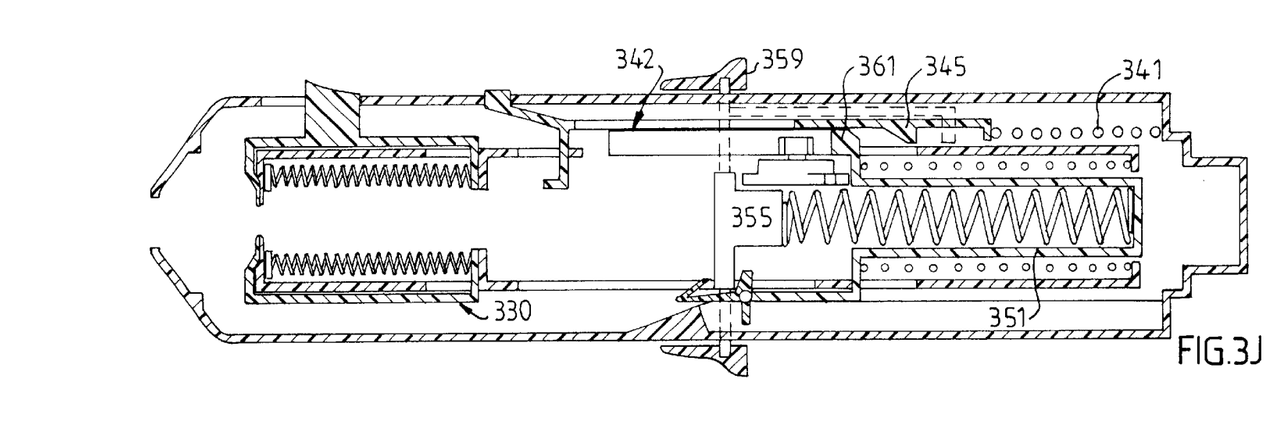

In FIG. 3A penetration head 342 is in a rear cocked position retained by trigger 344 locked to the housing. The penetration drive spring 341 is compressed. The contact surface 343 of the penetration head 342 is located in a rear position allowing for insertion of different syringe sizes with different distances to the penetration head, as illustrated by the two fingergrip 324 positions shown. The penetration head dead run necessary for the shorter syringes is no problem since the separate penetration drive spring 341 need not be stronger than necessary for needle penetration and return spring 336 compression. Unaffected by the autopenetration mechanism 340 the return springs 336 push the carrier 330, syringe 320, remover 333 and autoinjection mechanism 350 to the retracted, needle hidden, position. The injection head 355 is kept in a start position relative the conveyor 351 by hook 353 and with injection drive spring 354 compressed. Also for the injection head 355 in this position there is a sufficient clearance to allow for different plunger positions due to differences in syringe sizes or filling degrees, which clearance is made possible in spite of the strong injection drive spring 354 as any excessive injection head 355 speed is prevented by damper 356. Spring 354 can be dimensioned for the largest force requirement contemplated for any syringe. In FIG. 3B button 335 of remover 333 has been moved forwards against springs 336, compressed between foundations 312 and rear flanges 338 of remover 333, whereby forward restriction 334 has freed needle cover 327 from syringe front part 322 while the syringe itself remains in the retracted position. In FIG. 3C button 335 has been released and the remover 333 unit has returned back under influence of return springs 336. The device is now ready for initiation. In FIG. 3D the trigger 344 has been pushed, the penetration drive spring 341 has moved penetration head 342 forwards to engage contact surface 343 with syringe fingergrip 324 (only the larger syringe is shown in this and subsequent Figures) and propel it forwards to the forward, needle 323 exposed, position. In doing so the whole aggregate of syringe 320, carrier 330, remover 333 and carrier support 339 with injection mechanism 350 moves forward and this penetration movement is highly independent of syringe size since all syringe fronts are located at the same position. Penetration head action on the syringe lowers the retention requirements for the syringe in the carrier seat although an alternative is to let the penetration head act on the carrier instead. Also shown is that head hook 353 has been tilted by control structure 313, thereby freeing injection head 355 for forward motion relative conveyor 351. In FIG. 3E injection head 355 has moved forward with respect to conveyor 351 under influence of injection drive spring 354 to push plunger 326 to an intermediate position. Under his movement damper 356 is active as it moves axially together with the injection head 355 while its rotor part 358 is forced to rotate when moving along toothed rail 352. In FIG. 3F the syringe 320 is empty and injector head 355 and plunger 326 stop. Also the damper 356 stops resulting in an elimination of damper friction and an increase in injection drive spring 354 force acting between the injection head 355, and thereby carrier 330 with support 339, and conveyor 351. In FIG. 3G this force increase has resulted in that conveyor 351 has moved back with respect to carrier 330, as best seen in relation to the rear support 339 part, against the force of the weaker counterspring 360. This movement causes structure 361 on the conveyor 351 to affect tapering surface 345 on penetration head 342 to displace the rear part of penetration head 342 laterally and out of engagement with penetration drive spring 341. Carrier 330 with connected parts is now influenced only by force from the return springs 336. In FIG. 3H the return springs 336 has moved the carrier 330 rearwards to the needle hidden position for the syringe 320. Together with the carrier 330 also the injection mechanism 350 and the penetration head 342 has moved rearwards. In FIG. 3I cocking handle 359 has been pressed rearwards to move injection head 355 against injection drive spring 354 into a cocked position and head hook 353 again flex back to retain the injection head 355 in this position. The cocking movement also acts to compress penetration drive spring 341 via pusher 362 and make trigger 344 lock against housing 310. A ratchet mechanism (not shown) is arranged to disconnect the damper at rearward movements between injection head 355 and conveyor 351 to facilitate the cocking operation. In FIG. 3J the cocking handle 359 has been released, conveyor 351 and injection head 355 has returned to their initial positions with respect to carrier 330, thereby separating structure 361 and tapering surface 345, allowing the rear part of penetration head 342 to flex laterally into engagement with penetration drive spring 341. The device is now ready for cycle repetition and the syringe has been removed for replacement.

Figure 4:
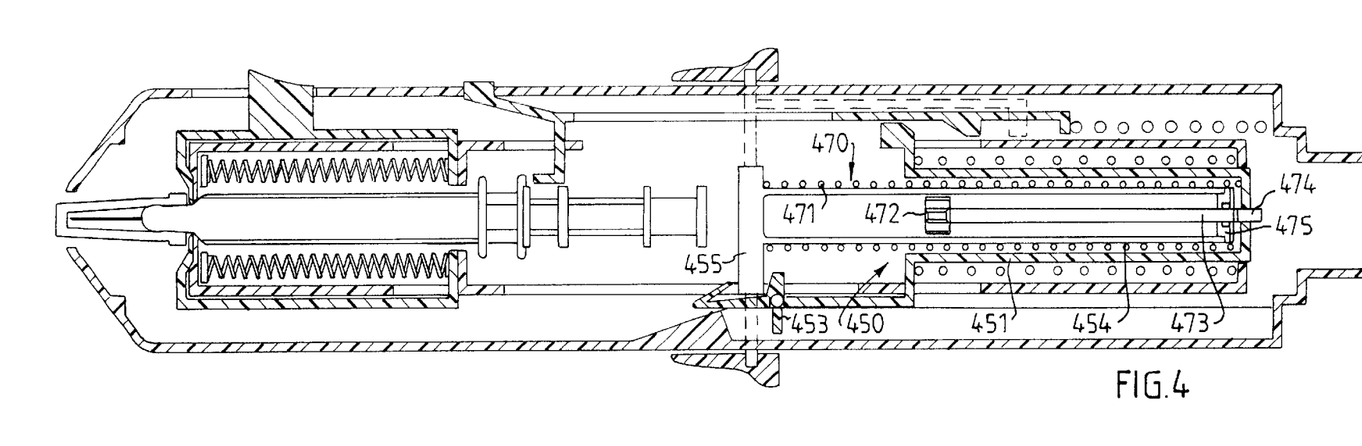
FIG. 4 shows a modification of the autoinjector of FIG. 3 in which a linear damper is used.

FIG. 4 illustrates a modification of the device of FIG. 3, which is identical in all aspects except that the rotational damper in the embodiment of FIG. 3 has been replaced with a linear viscous damper. As in FIG. 3 the autoinjection mechanism 450 comprises a conveyor 451 (but no toothed rail), a head hook 453, an injection drive spring 454 and an injection head 455. The linear damper, generally designated 470, comprises a cylinder 471, here showed as an integral part of the injection head 455, and a piston 472 attached to a plunger 473, which is attached to the conveyor 451 base at 474. A closure 475 with sealing for the plunger 473 closes the interior of the damper 470, containing an oil for controlled damping in flow restrictions in or around the piston 472. The piston also incorporates a one way valve arrangement (not shown) allowing undamped movement during the cocking procedure. The damper cylinder 471 is inserted, and utilizes the space, within the helical injection drive spring 454. The damper 470 operates in the same manner as that described in relation to FIG. 3, i.e. its cylinder/piston parts only move when injection head 455 moves relative conveyor 451 and performs a damping action only for forward injection head movements whereas the one way valve arrangement disconnect damping at rearward movements of the head.

What is claimed is:

1. An autoinjector for replaceable syringe containers comprising a barrel, a front opening with or for an injection needle and at least one movable rear piston, optionally with a plunger connected thereto, inserted in the barrel for the displacement of a container content, the autoinjector comprising a) a housing, b) a container carrier, arranged for reception of a container and arranged movably in relation to the housing in a container axial direction between a rear, needle-covering position and a forward, needle-exposing, position, c) an autopenetration mechanism comprising at least a penetration head and penetration drive, the penetration head being arranged for movement of the barrel or carrier in the forward direction and the penetration drive being operable to apply force between the housing and the penetration head;

d) an autoinjection mechanism comprising at least an injection head and an injection drive, the injection head being arranged for movement of a piston or plunger in the forward direction about the injection drive being operable to apply force between the housing of the carrier and the injection head, e) optionally an autoreturn mechanism operable to apply force between the housing and the barrel or carrier for movement thereof in the rearward direction, f) a control system for sequencing the operation of at least the autopenetration and autoinjection mechanism and a releasable injection lock for the autoinjection mechanism, and g) at least one damper arranged for energy absorption from the autopenetration and/or autoinjection movement.

2. The autoinjector of claim 1, wherein the damper is included in the penetration head.

3. The autoinjector of claim 2, wherein the damper includes a spring arranged in the axial direction, and further wherein the spring force is weaker than the force of the penetration drive.

4. The autoinjector of claim 3, wherein the penetration head comprises at least two parts between which the spring is arranged.

5. The autoinjector of claim 4, wherein the control system is arranged to enable the autoinjectin mechanism at relative movement between the two parts of the penetration head.

6. The autoinjector of claim 1, wherein the damper is included in the injection head.

7. The autoinjector of claim 6, wherein at least a part of the injection head is resilient and is operable as a damper.

8. The autoinjector of claim 1, wherein the damper is a viscous damper arranged to retard the autoinjection movement.

9. The autoinjector of claim 8, wherein the viscous damper retardation dominates over syringe flow restrictions.

10. The autoinjector of claim 8, wherein the autopenetration movement is unretarded or is at least less retarded than the autoinjection movement.

11. The autoinjector of claim 8, wherein the viscous damper is connected, directly or indirectly, between the penetration head and the injection head, to act at relative motions therebetween.

12. The autoinjector of claim 8, wherein the viscous damper is arranged in parallel with the injection head movement.

13. The autoinjector of claim 8, wherein the penetration drive is separate from, and provides a less strong force than, the injection drive.

* * * * *

UNITED STATES PATENT AND TRADEMARK OFFICE
CERTIFICATE OF CORRECTION

PATENT NO.    : 6,371,939 B2
DATED         : April 16, 2002
INVENTOR(S)   : Thomas Bergens et al.

It is certified that error appears in the above-identified patent and that said Letters Patent is hereby corrected as shown below:

Column 18,
Line 13, change "the forward direction about" to -- the forward direction and --.
Line 20, after "the autopenetration and autoinjection" insert -- mechanisms, comprising a releasable penetration lock for the autopenetration --.
Line 36, change "autoinjectin" to -- autoinjection --.

Signed and Sealed this

Twenty-third Day of July, 2002

Attest:

Attesting Officer

JAMES E. ROGAN
Director of the United States Patent and Trademark Office